(12) United States Patent
Stokes

(10) Patent No.: US 6,968,234 B2
(45) Date of Patent: Nov. 22, 2005

(54) IMPLANTABLE MEDICAL DEVICE HAVING BIOLOGICALLY ACTIVE POLYMERIC CASING

(75) Inventor: Kenneth B. Stokes, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 370 days.

(21) Appl. No.: 10/131,428

(22) Filed: Apr. 25, 2002

(65) Prior Publication Data

US 2003/0204229 A1    Oct. 30, 2003

(51) Int. Cl.$^7$ ............................................. A61N 1/362
(52) U.S. Cl. ........................................................ 607/36
(58) Field of Search ................................... 607/1–156

(56) References Cited

U.S. PATENT DOCUMENTS

| | | | |
|---|---|---|---|
| 5,043,278 A | 8/1991 | Nagaoka et al. | |
| 5,217,493 A | 6/1993 | Raad et al. | .................... 623/11 |
| 5,322,520 A | 6/1994 | Milder | ........................ 604/265 |
| 5,498,248 A | 3/1996 | Milder | ........................ 604/265 |
| 5,589,563 A | 12/1996 | Ward et al. | |
| 5,725,817 A | 3/1998 | Milder | ........................ 264/104 |
| 5,752,941 A | 5/1998 | Romano' et al. | ........... 604/265 |
| 5,755,758 A | 5/1998 | Woloszko et al. | .......... 607/116 |
| 5,834,051 A | 11/1998 | Woloszko et al. | ......... 427/2.24 |
| 5,895,563 A | 4/1999 | Muranushi | .................... 205/210 |
| 5,939,576 A | 8/1999 | Lichtenhan et al. | ........ 556/460 |
| 5,945,457 A * | 8/1999 | Plate et al. | .............. 514/772.1 |
| 6,017,334 A | 1/2000 | Rawls | ........................ 604/265 |
| 6,033,719 A * | 3/2000 | Keogh | ........................ 427/2.12 |
| 6,060,000 A | 5/2000 | Milder et al. | ................ 252/510 |
| 6,167,886 B1 | 1/2001 | Engel et al. | ................. 128/885 |
| 6,190,407 B1 | 2/2001 | Ogle et al. | ................... 623/1.51 |
| 6,193,752 B1 | 2/2001 | Hildebrandt | ............. 623/11.11 |
| 6,245,056 B1 | 6/2001 | Walker et al. | ............... 604/539 |
| 6,267,782 B1 | 7/2001 | Ogle et al. | .................... 623/1.1 |
| 2001/0049422 A1 | 12/2001 | Phaneuf et al. | |
| 2002/0022046 A1 | 2/2002 | Tedeschi et al. | |

FOREIGN PATENT DOCUMENTS

| | | | | |
|---|---|---|---|---|
| WO | WO 98/23306 | | 6/1998 | ........... A61L 27/00 |
| WO | WO 02/085425 A1 | | 10/2002 | ........... A61L 33/00 |

OTHER PUBLICATIONS

Crossley, G.H., "Cardiac Pacing Leads," vol. 18, No. 1, p. 95-112 (Feb. 2000).

(Continued)

Primary Examiner—Scott M. Getzow
(74) Attorney, Agent, or Firm—Girma Wolde-Michael; Michael C. Soldner

(57) ABSTRACT

An implantable medical device has a medical unit, such as a pacemaker lead, and a casing at least partially enclosing the medical unit. The casing is formed of a base polymer such as a polyurethane, a polyurethane copolymer, a fluoropolymer and a polyolefin or a silicone rubber. The casing has biologically active agents covalently bonded to the base polymer. The biologically active agents can be attached to the base polymer as surface active end groups. As an alternative, the biologically active may be attached to a backbone the base polymer. As yet a further alternative, the biologically active agents may be attached to surface modifying end groups, which are in turn attached to the base polymer. Examples of suitable biologically active agents are microbial peptide agents, detergents, non-steroidal anti-inflammatory drugs, cations, amine-containing organosilicones, diphosphonates, fatty acids and fatty acid salts.

4 Claims, 1 Drawing Sheet

OTHER PUBLICATIONS

Saito, N. et al., "Photochemical Grafting of α-Propylsulphate-Poly(ethylene oxide) on Polyurethane Surfaces and Enhanced Antithrombogenic Potential," *Biomaterials*, vol. 18, No. 17, p. 1195-1197 (1997).

An, Y. & Richard Friedman, "Concise Review of Mechanisms of Bacterial Adhesion to Biomaterial Surfaces", *J Biomed Mater Res*, 43: pp 338-348, 1998.

Byrd et al., "Intravascular Extraction of problematic or Infected Permanent Pacemaker Leads", *Pacing and Clinical Electrophysiology*, vol. 22, No. 9, pp. 1348-1357, Sep. 1999.

Wagener et al., "Chiral Polyolefins Bearing Amino Acids", *Macromolecules 34*, 7920-7922, 2001.

Wagener et al., "Perfect Comb' ADMET Grafted Copolymers", *Macromolecules 34*, 6845-6849, 2001.

* cited by examiner

IMPLANTABLE MEDICAL DEVICE HAVING BIOLOGICALLY ACTIVE POLYMERIC CASING

INCORPORATION BY REFERENCE

This application incorporates by reference the contents of U.S. Pat. No. 5,895,563 to Ward et al., issued Dec. 31, 1996.

BACKGROUND OF THE INVENTION

It has become common to treat many diseases using implantable medical devices (IMDs) that are chronically implanted within the body of a patient. Examples of such medical devices include pacemakers, defibrillators, drug-delivery devices, and electro-stimulators for stimulating nerves, muscles, and other tissue.

In spite of all precautions, bacterial colonization of implanted medical devices remains a serious complication. For pacemaker leads, for example, it is believed that about 10% of leads will fail or become infected, requiring removal. In approximately 27% of the operations to remove pacemaker leads, infection is reason for removal. Chronic pacemaker lead-centered infections can occur and can lead to serious complications including death. The literature overwhelmingly indicates that where possible, infected hardware must be removed in order to insure that the infection is cured.

Prevention of the infection in the first place would be a preferred alternative. The use of antimicrobial coatings on pacemaker leads not been successful for several reasons. One is that some patients can develop serious reactions to certain antimicrobial chemicals. Another is that lead centered infections typically occur chronically, primarily after reintervention. That is, when an implantable medical device (IMD) in general, or pacemaker lead in particular, is implanted, the infection rate is very low. However, the infection rate rises significantly when the IMD is subsequently adjusted or renewed. For example, when a pacemaker is first implanted, the infection rate for the leads approaches zero. If there is reintervention to replace the pacemaker pulse generator, which is located within a fibrous tissue capsule, then infection at the leads and around the capsule is more likely. Given that most antimicrobial coatings involve elution of the drug, the coating becomes ineffective long before it is needed.

The use of silver ion has been promoted as bactericidal. Silver received a bad name because it apparently also inhibits the healing process, resulting in blood leakage around treated valve sewing rings, for example. No effective long-term means of preventing or reducing device centered infection has yet been described.

SUMMARY OF THE INVENTION

Accordingly, one possible object of the invention is to prevent or reduce infections centered at an implanted medical device.

This and other objects are accomplished by providing in an improved implantable medical device. The implantable medical device has a medical unit, such as a pacemaker lead, and a casing at least partially enclosing the medical unit. The casing is formed of a base polymer such as a polyurethane, a polyurethane copolymer, a fluoropolymer, a polyolefin or a silicone rubber. The casing has biologically active agents covalently bonded within or on the base polymer. The biologically active agents can be attached to the base polymer as surface modifying end groups (SME). As an alternative, the biologically active agent may be attached to the backbone of the base polymer. As yet a further alternative, the biologically active agents may be attached to surface modifying end groups, which are in turn attached to the base polymer.

Examples of suitable biologically active agents are microbial peptide agents, detergents, non-steroidal anti-inflammatory drugs, cations, amine-containing organosilicones, diphosphonates, fatty acids and fatty acid salts

BRIEF DESCRIPTION OF THE DRAWINGS

These and other objects and advantages of the present invention will become more apparent and more readily appreciated from the following description of the preferred embodiments, taken in conjunction with the accompanying drawing of which

DETAILED DESCRIPTION OF THE EMBODIMENTS

Figure 1:
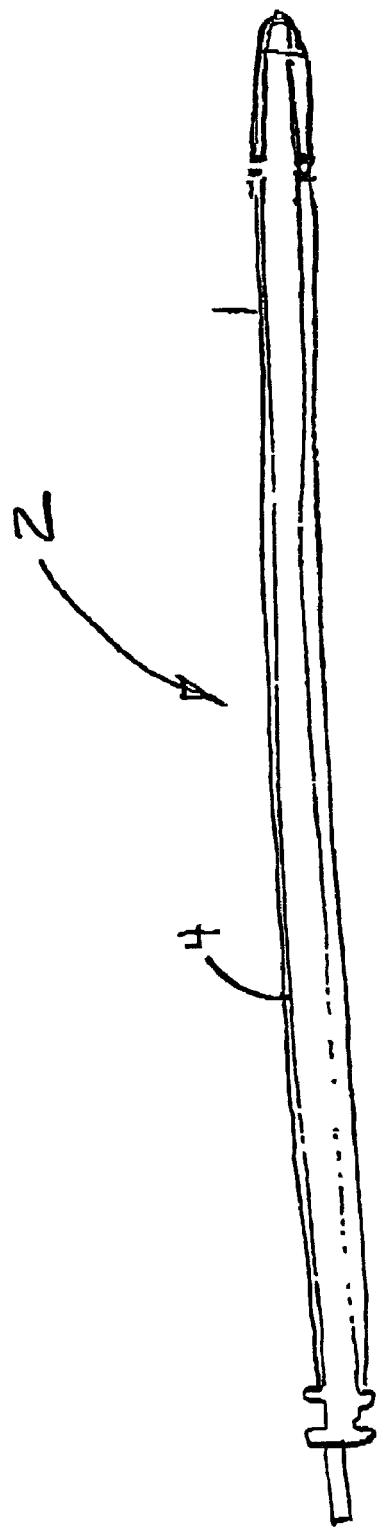
FIG. 1 is a cut away side view of a medical lead with insulation made from a polymer having surface modifying end groups.

One way to reduce infection at the implanted medical device (IMD) is to prevent the adhesion of the microorganism at the surface of the IMD. If the surface chemicals are changed or modified with a biologically active agent such as a microbial peptide agent, an antimicrobial agent such as those synthesized with quinolone drugs (e.g. Ciprofloxacin, Norfloxacin), an antibiotic such as Gentamyacin or Zithromax, a biocompatible detergent such as Pluronic® brand PE-EO block polymer sold by BASF, a non-steroidal anti-inflammatory drug, a cation, an amine-containing organosilicone, a fatty acid or a fatty acid salt, bacterial adhesion to the surface of the IMD is discouraged. It is proposed that polyurethane and silicone rubber polymers used in bradycardia, tachycardia and neurological leads can be modified using certain adhesion reducing surface modifying end groups such as a detergent, salicylic acids such as aspirin or ibuprofin (non-steroidal anti-inflammatory agents), fatty acid salts (cations) or amine-containing silicones, bacterial adhesion will be reduced acutely, chronically, and many years later when the pulse generator is changed-out. Such agents may also have a significant benefit in preventing scar tissue adhesion to facilitate chronic removal. It is also proposed that antimicrobial agents may not elicit an immune response in susceptible individuals if the agent is covalently bonded (as a surface modifying end ("SME")) to a device surface.

The inventors propose a polymer coating for implantable medical devices, which polymer coating includes biologically active agents.

FIG. 1 is a side cutaway view of a medical lead according to one aspect of the invention. The lead includes an elongated lead body 2, which is covered over at least a portion of its surface with a coating 4. Note that the lead has an insulation which may be made entirely of the SME polymer or it could have an SME polymer applied as a coating on the insulation. The coating 4 is formed of a polymer having biologically active agents. Although a lead is shown for discussion purposes, it will be understood that the surface of other IMDs may be used, including surfaces of catheters, stents, drug delivery devices, etc.

The coating 4 is formed of a polymeric material, which is described below. The coating may be formed as the outer casing of the IMD. Alternatively, the IMD may have a shell formed of a polymeric or non-polymeric material. In this case, the coating may be formed on the shell.

It is not necessary for the coating to completely encapsulate the IMD. The coating may be formed only on surfaces where infection is likely or only on surfaces that do not require a patient-IMD interface. For example, the electrodes of a pacemaker lead likely could not be encapsulated with the coating.

The polymeric material includes a base polymer having biologically active agents thereon. Many different polymers can be used as the base polymer. For example, silicone rubbers, fluoropolymers, epoxies, polyamides, polyimides, polyolefins, polyurethanes, polyurethane copolymers such as polyether polyurethanes, polycarbonate polyurethanes, silicone polyurethane and the like, may be used.

There are at least three ways to attach the biologically active agent to the base polymer. First, biologically active agent can be attached as a surface modifying end group to the base polymer. Second, the biologically active agent can be attached to the backbone of the base polymer. Third, the biologically active agent can be attached to a different surface modifying end group, which is in turn attached to the base polymer.

With regard to the first method, attaching the biologically active agent to the base polymer as a surface modifying end group, U.S. Pat. No. 5,895,563 to Ward et al., issued on Dec. 31, 1996 discloses a method of attaching surface active end groups to base polymers for use in biological materials. The base polymer may be linear. The surface active end groups may be covalently bonded to the base polymer. Ward et al. uses the surface active end groups to achieve a surface or interfacial tension that differs by at least 1 dyne/cm from the surface or interfacial tension of an otherwise identical polymer that does not contain said covalently bonded surface active end groups. The method of Ward et al. can be used to attach the biologically active agent to the base polymer as a surface modifying end group.

When the biologically active agent is attached directly to the base polymer as a surface modifying end group, the biologically active agent is permanently (covalently) fixed on the base polymer. As will be described below, it is also possible to attach the biologically active agent to the base polymer such that the biologically active agent is released upon the occurrence of certain biological conditions indicative of infection.

The second way to attach the biologically active agent to the base polymer is to attach it to the backbone of the base polymer. There are numerous different ways this can be done. For example, the biologically active agent can be grafted or branched onto the polymer using ADMET chemistry.

ADMET chemistry is described in Wagener et al. "Chiral Polyolefins Bearing Amino Acids", Macromolecules, 34, 7920–7922 (2001) and Wagener et al., "Perfect Comb ADMET Grafted Copolymers", Macromolecules, 34, 6845–6849 (2001). ADMET chemistry requires double bonds within the polymer backbone. The surface modifying agent attaches to the double bonds. Olefin metathesis chemistry can also be used to attach surface modifying agents to the backbone of the polymer. This process uses catalysts including molybdenum, tungsten, rhenium, ruthenium and alloys thereof. Olefin metathesis chemistry is described in U.S. Pat. No. 5,939,576 to Lichtenhan et al., for example.

The ADMET chemistry can be used to attach the biologically active agent to the backbone of the base polymer. For example, some biologically active agents, such as detergents and fatty acid salts, are cations. If a fatty acid salt is attached at the salt thereof, it will no longer have cation functionality. Therefore, biologically active agents such as fatty acid salts may lose their desirable biological properties if attached in this manner. Thus, it may be preferable to attach fatty acid salts using ADMET chemistry, which preserves the cation functionality. In this case the base polymer must have a double bond. This is ensured by proper polymer synthesis.

Other ways to attach the biologically active agent to the backbone of the base polymer employ sulfonate or amine functionality, for example.

A third way to attach the biologically active agent to the base polymer is by attaching the biologically active agent to a surface modifying end group, which is in turn attached to the base polymer. The surface modifying end group is attached according to the methodology described in U.S. Pat. No. 5,895,563. There are a plurality of ways to attach the biologically active agent to the surface modifying end groups. The surface modifying end groups could be chosen such that the terminal end group thereon matches the functionality of the biologically active agent and allow the surface modifying end groups to fuse with the biologically active agent. ADMET chemistry can be used to attach the biologically active agent to the surface modifying end groups as long as the surface modifying end groups have a double bond. That is, ADMET chemistry breaks the double bond and attaches the biologically active agent at this point. Linoleic acid and linoleic acid are two examples of SME groups that have a double bond. Thus, linoleic acid and linolenic acid could both be used to retain a biologically active agent. Attachment can also be performed through sulfonate or amine functionality, for example.

Polyethylene oxides (PEOs) are a surface modifying end group that may be particularly useful for retaining biologically active agents. PEOs break off the base polymer due to oxidation when there is cellular inflammation (when the IMD is attacked by macrophages). When the PEO is released, the biologically active agent is delivered to the infection.

It should be noted that it may be desirable to attach more than one different biologically active agent to the surface modifying end group. For example, a polyurethane heart valve having a diphosphonate biologically active agent and an antimicrobial biolocically active agent could be made.

Inhibition of calcification in bioprosthetic heart valves using sustained local release of calcium and sodium diphosphonates has been reported. However, phosphonates released systemically can have adverse effects on overall growth, bone development and calcium metabolism. Immobilization of ethanehydroxydiphosphonate within a bioprosthetic heart valve as the poorly soluble $Ca^{2+}$ salt inhibits calcification at drug levels insufficient to produce side effects. However, rapid time-dependent efflux of the phosphonate from the pericardial tissue limited its usefulness in long-term heart valve replacements. The use of diphosphonates as SMEs or attached to SMEs such as PEO, hydrocarbon, silicone or fluorocarbon, etc. will control mineralization of silicone rubber pacemaker leads, enhancing their chronic extractability.

Another use for diphosphonates is in heart valves. Specifically, polymeric heart valves have not been used because of thrombosis. A plastic heart valve could experience mineralization and infection. If a leaflet heart valve were made of polyurethane, with diphosphonate attached to the polyurethane, then mineralization would not be a problem.

The invention has been described in detail with particular reference to preferred embodiments thereof and examples, but it will be understood that variations and modifications can be effected within the spirit and scope of the invention.

What is claimed is:

1. An implantable medical device, comprising:
a medical unit for long term implantation in a subject; and
a casing at least partially enclosing the medical unit, the casing comprising a base polymer selected from the group consisting of polyurethanes, polyurethane copolymers, fluoropolymers, polyolefins, epoxies and silicone rubbers, a polythylene oxide surface modifying end group covalently bonded to the base polymer, and a biologically active agent attached to the surface modifying end group selected from a group consisting of microbial peptide agents, antibiotics, detergents, non-steroidal anti-imflammatory drugs, cations, amine-containing organosilicones, diphosphonates, fatty acids, fatty acid salts, and wherein the biologically active agent is released in the presence of biological conditions indicative of infection by the polyethylene oxide surface modifying end group breaking off the base polymer due to oxidation casued by cellular inflammation attendant an attack by macrophages.

2. An implantable medical device according to claim 1, wherein the medical unit comprises one of: a pacemaker lead, a defibrillation lead, a neurological stimulation lead, a combination pacing and defibrillation lead, an artificial heart valve.

3. An implantable medical device according to claim 1, wherein
the medical unit furthur comprises a shell having an outer surface, and
the casing is formed on at least a portion of the outer surface of the shell.

4. An implantable medical device according to claim 1, wherein at least two different biologically active agents are attached to the base polymer.

* * * * *